United States Patent [19]
Cettina et al.

[11] Patent Number: 5,824,324
[45] Date of Patent: Oct. 20, 1998

[54] PERSONAL LIQUID CLEANSER PRODUCT WITH PARTICULATE BICARBONATE SUSPENSION PHASE

[75] Inventors: Melinda Cettina, Robbinsville; Wolfgang R. Bergmann, Princeton, both of N.J.

[73] Assignee: Church & Dwight Co., Inc.

[21] Appl. No.: 744,526

[22] Filed: Nov. 6, 1996

[51] Int. Cl.⁶ .............................. A61K 7/00; C11D 1/755
[52] U.S. Cl. ............... 424/401; 252/174.15; 252/174.17; 252/550; 252/551; 252/554; 252/555; 252/DIG. 2; 252/DIG. 13
[58] Field of Search ............................ 424/401; 252/550, 252/174.15, 174.17, 551, 554, 555, DIG. 2, DIG. 13

[56] References Cited

U.S. PATENT DOCUMENTS

| | | |
|---|---|---|
| 3,957,970 | 5/1976 | Korkis . |
| 4,741,855 | 5/1988 | Grote et al. . |
| 4,788,006 | 11/1988 | Bolich et al. ............................ 252/550 |
| 4,948,576 | 8/1990 | Verdicchio et al. . |
| 5,085,857 | 2/1992 | Reid et al. . |
| 5,372,751 | 12/1994 | Rys-Cicciari et al. . |
| 5,478,490 | 12/1995 | Russo et al. . |
| 5,514,369 | 5/1996 | Salka et al. . |

*Primary Examiner*—Thurman K. Page
*Assistant Examiner*—Kathryne E. Shelborne
*Attorney, Agent, or Firm*—Irving Fishman

[57] ABSTRACT

This invention provides a fluid detergent formulation which is particularly suitable for application as a personal cleanser for bath or shower usage. An invention fluid cleanser composition is an aqueous formulation which can be utilized as a mild body shampoo with skin cleansing and skin conditioning benefits. An important feature of an invention fluid cleanser composition is a stable suspension phase of particulate alkali metal bicarbonate which functions as a buffering agent, and which provides deodorizing, exfoliating and water-softening benefits for skin conditioning.

13 Claims, No Drawings

PERSONAL LIQUID CLEANSER PRODUCT WITH PARTICULATE BICARBONATE SUSPENSION PHASE

BACKGROUND OF THE INVENTION

The present invention generally relates to personal fluid cleansing products which are in the form of a stabilized aqueous medium, and which can be utilized as a mild body shampoo with skin cleansing and skin conditioning benefits.

Detergent and cleansing compositions intended for use as personal cleansing products ideally must exhibit good cleansing and foam characteristics, and they must have low irritation potential to the skin and the eyes.

Skin is made up of several layers of cells which coat and protect the keratin and collagen fibrous proteins that form the skeleton of its structure. The outermost of these layers (the stratum corneum) is known to be composed of 250 Å diameter protein bundles surrounded by 80 Å thick bilayers of epidermal lipids and water. Surfactants can penetrate the stratum corneum membrane and destroy its integrity by delipidization. This can cause skin irritation, and lead to dry rough skin.

Synthetic surface active agents which are used in personal cleansing compositions include anionic, cationic, amphoteric and nonionic surfactants.

The surfactants generally exhibiting the more superior properties in terms of foaming, cleaning and end result attributes are the anionic detergents. Thus, most detergent and cleansing formulations intended for personal use contain anionic surfactants as one of the active ingredients. These surfactants, however, have a tendency to be very irritating to the skin and the eyes in the levels normally utilized, i.e., above 10% by weight of the total composition. For this reason, detergent compositions containing anionic surfactants intended for personal use are modified by substituting a significant amount of nonionic surfactants which are generally mild although of less effective foaming and cleansing ability. Certain amphoteric surfactants also are known to have a low eye irritation potential.

Ideal cosmetic cleansers should cleanse the skin gently, cause little or no irritation, and not defat and dry the skin. Most lathering soaps, liquids and bars fail in this respect, and most current cleansing products do not deliver an adequate moisturizing benefit during cleansing.

Accordingly, it is an object of this invention to provide an improved cleansing composition for personal usage.

It is another object of this invention to provide a fluid detergent composition which is adapted for cleansing and conditioning the skin, and which exhibits foaming properties.

It is a further object of this invention to provide an aqueous cleansing formulation which has a content of alkali metal bicarbonate, and which exhibits low irritation potential to the eyes and skin.

Other objects and advantages shall become apparent from the accompanying description and examples.

Publications of background interest relative to the present invention include U.S. Pat. Nos. 3,957,970; 4,741,855; 4,948,576; 5,085,857; 5,372,751; 5,478,490; and 5,514,369; incorporated by reference.

DESCRIPTION OF THE INVENTION

One or more objects of the present invention are accomplished by the provision of a fluid, preferably liquid, cleanser composition of ingredients comprising (1) between about 2–60 weight percent of surfactant; (2) between about 5–50 weight percent of alkali metal bicarbonate or carbonate; (3) between about 1–10 weight percent of suspending agent; and (4) between about 10–60 weight percent of water; wherein the composition has a pH between about 7–10.5, and a viscosity in the range between about 1000–145,000 centipoises.

The surfactant ingredient of a present invention fluid cleanser composition can be selected from the group consisting of anionic, cationic, amphoteric and alkylglycosidic surface active agents. Suitable surfactants for purposes of the present invention are elaborated in references such as U.S. Pat. Nos. 4,902,499, 4,948,576, and 5,514,369; incorporated by reference. A preferred content of surfactant ingredient is between about 2–30 weight percent.

One class of anionic surfactants are alkyl and alkyl ether sulfates, such as sodium cocoalkyl triethylene glycol ether sulfate.

Another class of anionic surfactants are the water-soluble salts corresponding to the formula $R_1$—$SO_3$—M, where $R_1$ is a $C_8$–$C_{24}$ aliphatic group, and M is a cation.

Another class of anionic surfactants are the reaction products of fatty acids esterified with isethionic acid and neutralized with an alkaline reagent.

Another class of anionic surfactants are sulfosuccinate salts such as disodium N-octadecylsulfosuccinamate and sodium dioctyl sulfosuccinate.

Another class of anionic surfactants are olefin sulfonates, such as those described in U.S. Pat. No. 3,332,880; incorporated by reference.

Suitable nonionic surfactants broadly include compounds produced by the condensation of alkylene oxide with an organic hydrophobic compound which can be either aliphatic, alicyclic or aromatic in structure.

Nonionic surfactants are illustrated by polyethylene oxide condensates of $C_6$–$C_{12}$ alkylphenols; condensates of ethylene oxide with the reaction product of propylene oxide and ethylenediamine; long chain tertiary amine oxides; long chain tertiary phosphine oxides; long chain dialkyl sulfoxides; and the like.

Suitable cationic surfactants are compounds containing positively charged amine or quaternary ammonium groups, such as those described in U.S. Pat. Nos. 3,155,591, 3,929,678, 3,959,461, 4,387,090, and the like; incorporated by reference.

Suitable amphoteric surfactants include derivatives of aliphatic quaternary ammonium, phosphonium and sulfonium compounds.

One class of amphoteric surfactants are zwitterionic compounds such as betaines, sultaines and phosphobetaines. Illustrative of a betaine is cocoamidopropyl betaine.

Another class of amphoteric surfactants are compounds containing an amine group and an anionic group such as carboxylate, sulfonate, sulfate, phosphate or phosphonate, as illustrated by sodium 3-dodecylaminopropionate and sodium 3-dodecylaminopropane sulfonate.

Another class of suitable surfactants are alkyl polyglycosides, such as APG 25, APG 300, Glucopon 600 and Plantaren 2000, which are tradename products sold by the Henkel Corporation, Ambler, Pa.

The bicarbonate or carbonate ingredient of a present invention fluid cleanser composition can be selected from the group consisting of sodium bicarbonate, potassium bicarbonate, sodium carbonate and potassium carbonate, and mixtures thereof. Typically, the bicarbonate or carbonate ingredient of the fluid cleanser composition has an average particle size between about 10–250 microns. The average particle size preferably is between about 10–200 microns, and most preferably between about 20–50 microns. A preferred content of bicarbonate or carbonate ingredient is between about 7–40 weight percent.

Because the particulate bicarbonate or carbonate salt ingredient is in a suspension phase, a large proportion can be incorporated without the limitation of solubility in the fluid medium. The particulate bicarbonate or carbonate salt also serves as a mild exfoliant when in contact with a skin surface.

Sodium bicarbonate is sold by Church & Dwight Co., Inc. (Princeton, N.J.) with different average particle sizes, such as Grade 1 (about 55 microns) and Grade 3 (about 25 microns).

The suspending agent ingredient of a present invention fluid cleanser composition preferably is selected from long chain acyl derivatives such as a glycol ester, which also can contribute a pearlescence effect to the composition. Illustrative of suitable suspending agents are ethylene glycol monostearate and distearate. Other useful suspending agents include fatty acid alkanol amides such as stearic monoethanolamide; $C_{16}$–$C_{22}$ alkyl dimethylamine oxides such as stearyl dimethylamine oxide, fatty amides such as dihydrogenated tallow phthalic acid amide; and the like. Suspending agents are described in U.S. Pat. No. 5,439,682; incorporated by reference. Up to about 3 weight percent of auxiliary thickeners can be added to supplement suspending power.

In another embodiment this invention provides a fluid cleanser composition of ingredients comprising (1) between about 2–60 weight percent of surfactant; (2) between about 5–50 weight percent of alkali metal bicarbonate or carbonate; (3) between about 1–10 weight percent of suspending agent; (4) between about 10–60 weight percent of water; and (5) between about 0.05–3 weight percent of thickening agent; wherein the composition has a pH between about 7–10.5, and a viscosity in the range between about 1000–145,000 centipoises.

The thickening agent ingredient of a present invention liquid cleanser composition is selected from anionic, cationic and nonionic compounds which provide the desired viscosity, such as cellulosic derivatives and hydrocolloid gums.

Suitable thickening agents include hydroxymethyl cellulose, hydroxybutyl methyl cellulose, carboxymethyl cellulose, acrylated steareth-20 methacrylate copolymer (Acrysol ICS-1; Rohm and Haas), xanthan gum, guar gum, guar hydroxypropyltrimonium chloride (Jaguar C series, Rhone-Poulenc), and the like. Thickening agents are described in U.S. Pat. No. 5,439,682; incorporated by reference.

In another embodiment this invention provides a fluid cleanser composition of ingredients comprising (1) between about 2–60 weight percent of a surfactant; (2) between about 5–50 weight percent of alkali metal bicarbonate or carbonate; (3) between about 1–10 weight percent of suspending agent; (4) between about 10–60 weight percent of water; and (5) between about 0.1–5 weight percent of hydrophilic silicone-polymer; wherein the composition has a pH between about 7–10.5, and a viscosity in the range between about 1000–145,000 centipoises.

The hydrophilic silicone-polymer ingredient of a present invention fluid cleanser composition is selected from a specific structural type of silicone nonionic surfactant polymers, having multiple polyoxyalkylene sidechains which impart hydrophilic properties to the silicone-polymer ingredient.

The term "hydrophilic" as employed herein refers to a water-dispersible silicone-polymer ingredient which has a water-solubility of at least about two grams per one hundred grams of water at 25° C.

Illustrative of hydrophilic silicone-polymer ingredients are dimethicone copolyol type of polymers, which include commercial products such as Dow Corning 193, GE SF-1288, Abil B 8847 (Goldschmidt), Alkasil NE 58-50 (Rhone-Poulenc), Amersil DMC-287 (Americol), KF 353A (Shin Etsu), Masil 1066D (PPG/Mazer), Silicone Copolymer F-754 (Wacker), Sibwet L-7000 (Union Carbide), and the like, and similar hydrophilic silicone-polymers as listed in the CFTA International Cosmetic Ingredient Dictionary (Fourth Edition); incorporated by reference.

Other suitable hydrophilic silicone-polymers are exemplified by dihydroxy-endcapped polydimethylsiloxanes such as dimethacanol (GE Silicone SM 2725), and amine functionalized silicones such as GE Silicone SM 2658.

The hydrophilic silicone-polymer ingredient has a gelling effect, and increases the viscosity of the emulsified aqueous medium. Additionally, the hydrophilic silicone-polymer ingredient functions as a detackifier when the cleanser composition is applied to a skin surface, and it is a foam modifier and contributes to a smooth skin-feel.

A present invention fluid cleanser composition can include between about 0.1–5 weight percent of moisturizer as an additional ingredient. An ingredient such as propylene glycol, glycerol, dipropylene glycol or polyvinyl alcohol can function as a humectant when the cleanser composition is applied to a skin surface.

A present invention fluid cleanser composition also can include optional ingredients such as between about 0.1–3 weight percent of preservative, and between about 0.1–2 weight percent of fragrance.

Suitable preservatives include benzyl alcohol, methyl paraben, ethyl paraben, propyl paraben, imidazolidinyl urea, N-(3-chloroallyl)-hexaminium chloride (Dowicil 200, Dow Chemical Company), methylchloroisothiazolinone, benzalkonium chloride, and the like.

Suitable fragrances are exemplified by synthetic compounds and natural oils as described in U.S. Pat. Nos. 4,314,915; 4,411,829; and 4,434,306; incorporated by reference. Synthetic fragrances include geraniol, eugenol, linalool, phenethyl acetate, isobornyl acetate, and the like.

Other optional ingredients can be included in an invention fluid cleanser composition, such as colorant, pearlescent agent, anti-acne medicament (resorcinol), antioxidant, skin healing agent (allantoin), sequestrant, vitamin E, antidandruff agent (zinc pyridinethione), protein, foam booster, and the like.

Depending on the intended product end-use, a present invention cleanser composition can vary in rheology, from a relatively low viscosity liquid to a soft gel-like consistency.

A present invention cleanser composition can be prepared by standard procedures employed for liquid soap and shampoo product manufacture. As illustrated in the Examples, there is a preferred order of organic and inorganic ingredient blending to achieve stable and homogeneous fluid cleanser products.

The products of the present invention can be formulated as free-flowing liquids, dilatant liquids, thixotropic liquids, creams, pastes, and the like.

The following examples are further illustrative of the present invention. The components and specific ingredients are presented as being typical, and various modifications can be derived in view of the foregoing disclosure within the scope of the invention.

Example I

This Example illustrates the preparation of a fluid cleanser composition in accordance with the present invention.

The following ingredients are blended by following the procedure described below:

|  | Weight Percent |
| --- | --- |
| Steol CS 230[1] | 50.0 |
| Velvetex BA-35[2] | 10.0 |
| GE Silicone 407-2418[3] | 1.0 |
| Water(A) | 2.0 |
| Sodium bicarbonate[4] | 12.0 |
| Methocel J75MS[5] | 0.5 |
| Ethylene glycol distearate | 3.4 |
| Water(B) | 20.5 |
| Fragrance[6] | 0.6 |

[1]Sodium laureth sulfate (2 ethoxylates); 24.5–26.5% active; Stepan.
[2]Cocamidopropyl betaine; 30% active; Henkel.
[3]Dimethicone copolyol.
[4]Grade 3 (25 micron average); Church & Dwight.
[5]Hydroxypropyl methylcellulose; Dow Chemical.
[6]By-The-Sea RH-2771; Takasago.

Water(A) and silicone are admixed and stirred at room temperature until the silicone is dissolved.

Water(B), Methocel and one-half of the sodium bicarbonate are admixed in a reactor and heated to 80° C. The ethylene glycol distearate is added to the admixture with stirring until it is blended.

The temperature of the admixture in the reactor is lowered to 65° C. The remaining sodium bicarbonate, Velvetex and the separately prepared aqueous silicone solution are added to the reactor contents, followed by the addition of the Steol ingredient with stirring until the admixture is homogeneous.

The resultant mixture is cooled to 30° C., and the fragrance ingredient is added with stirring. The product has a pH of 8.93, and a viscosity of 64,800 centipoises[7].

[7]Measured 24 hour viscosity using a Brookfield viscometer with a RV spindle #6 at 5 rpm.

Example II

This Example illustrates the preparation of a fluid cleanser composition in accordance with the present invention.

The following ingredients are blended following the procedure described below:

|  | Weight Percent |
| --- | --- |
| Steol CS 230 | 50.00 |
| Velvetex BA-35 | 10.00 |
| GE Silicone 288[1] | 1.00 |
| Sodium bicarbonate | 20.00 |
| Methocel J75MS | 0.25 |
| Ethylene glycol distearate | 3.40 |
| Water | 13.85 |
| Fragrance[3] | 1.50 |

[1]Sodium laureth sulfate (2 ethoxylates); 24.5–26.5% active; Stepan.
[2]Cocamidopropyl betaine; 30% active; Henkel.
[3]Dimethicone copolyol.

The water, Methocel and one-half of the sodium bicarbonate are admixed in a reactor and heated to 80° C. The ethylene glycol distearate is added to the admixture with stirring until it is blended.

The temperature of the admixture in the reactor is lowered to 65° C. The Velvetex and silicone are added to the reactor contents. The temperature of the admixture is lowered to 50° C., and the remaining sodium bicarbonate is added, followed by the addition of the Steol ingredient with stirring until the admixture is homogeneous.

The resultant emulsion medium is cooled to 30° C., and the fragrance ingredient is added with stirring. The product has a pH of 8.5, and a viscosity of 18,720 centipoises[4].

[4]Measured 24 hour viscosity using a Brookfield viscometer with a RV spindle #6 at 5 rpm.

What is claimed is:

1. A fluid cleanser composition of ingredients consisting essentially of (1) between about 2–60 weight percent of surfactant; (2) between about 5–50 weight percent of a stable suspension phase of alkali metal bicarbonate or carbonate which comprises sodium bicarbonate, potassium bicarbonate, sodium carbonate or potassium carbonate or any mixture thereof having an average particle size between about 10–250 microns; (3) between about 1–10 weight percent of suspending agent; and (4) between about 10–60 weight percent of water; wherein the composition has a pH between about 7–10.5, and a viscosity in the range between about 1000–145,000 centipoises.

2. A cleanser composition in accordance with claim 1 wherein the surfactant is selected from the group consisting of anionic, cationic, amphoteric and alkylglycoside surface active agents.

3. A cleanser composition in accordance with claim 1 wherein the suspending agent comprises a glycol ester or fatty amide.

4. A cleanser composition in accordance with claim 1 which additionally contains between about 0.1–5 weight percent of moisturizer.

5. A cleanser composition in accordance with claim 1 which additionally contains between about 0.1–5 weight percent of alkylene glycol moisturizer.

6. A cleanser composition in accordance with claim 1 which additionally contains between about 0.1–3 weight percent of preservative.

7. A cleanser composition in accordance with claim 1 which additionally contains between about 0.1–2 weight percent of fragrance.

8. A fluid cleanser composition of ingredients consisting essentially of (1) between about 2–60 weight percent of surfactant; (2) between about 5–50 weight percent of a stable suspension phase of alkali metal bicarbonate or carbonate which comprises sodium bicarbonate, potassium bicarbonate, sodium carbonate or potassium carbonate or any mixture thereof having an average particle size between about 10–250 microns; (3) between about 1–10 weight percent of suspending agent; (4) between about 10–60 weight percent of water; and (5) between about 0.05–3 weight percent of thickening agent; wherein the composition has a pH between about 7–10.5, and a viscosity in the range between about 1000–145,000 centipoises.

9. A cleanser composition in accordance with claim 8 wherein the thickening agent is a cellulosic derivative.

10. A cleanser composition in accordance with claim 8 wherein the thickening agent is a hydrocolloid gum.

11. A fluid cleanser composition of ingredients comprising (1) between about 2–60 weight percent of surfactant; (2) between about 5–50 weight percent of a stable suspension phase of alkali metal bicarbonate or carbonate which comprises sodium bicarbonate, potassium bicarbonate, sodium carbonate or potassium carbonate or any mixture thereof having an average particle size between about 10–250 microns; (3) between about 1–10 weight percent of suspending agent; (4) between about 10–60 weight percent of water; and (5) between about 0.1–5 weight percent of a silicone component, wherein the silicone component consists of a hydrophilic silicone-polymer; wherein the composition has a pH between about 7–10.5, and a viscosity in the range between about 1000–145,000 centipoises.

12. A cleanser composition in accordance with claim 11 wherein the silicone-polymer is dimethicone copolyol, dihydroxy-endcapped polydimethylsiloxane or amine functionalized silicone.

13. A fluid cleanser composition of ingredients comprising (1) between about 2–60 weight percent of surfactant; (2) between about 5–50 weight percent of a stable suspension phase of alkali metal bicarbonate or carbonate which comprises sodium bicarbonate, potassium bicarbonate, sodium carbonate or potassium carbonate or any mixture thereof having an average particle size between about 10–250 microns; (3) between about 1–10 weight percent of suspending agent; (4) between about 10–60 weight percent of water; (5) between about 0.05–3 weight percent of thickening agent; and (6) between about 0.1–5 weight percent of a silicone component, wherein the silicone component consists of a hydrophilic silicone-polymer; wherein the composition has a pH between about 7–10.5, and a viscosity in the range between about 1000–145,000 centipoises.

\* \* \* \* \*